(12) United States Patent
Fain

(10) Patent No.: US 7,149,569 B1
(45) Date of Patent: Dec. 12, 2006

(54) APPARATUS AND METHOD FOR IMPROVED MORPHOLOGY DISCRIMINATION IN AN IMPLANTABLE CARDIOVERTER DEFIBRILLATOR

(75) Inventor: Eric S. Fain, Menlo Park, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 122 days.

(21) Appl. No.: 10/737,232

(22) Filed: Dec. 15, 2003

(51) Int. Cl.
*A61B 5/04* (2006.01)

(52) U.S. Cl. .................................... 600/515

(58) Field of Classification Search ............... 600/515, 600/518; 607/14
See application file for complete search history.

(56) References Cited

U.S. PATENT DOCUMENTS

| | | | |
|---|---|---|---|
| 4,830,006 A | 5/1989 | Haluska et al. | 128/419 PG |
| 5,240,009 A | 8/1993 | Williams | 128/702 |
| 5,779,645 A | 7/1998 | Olson et al. | 600/518 |
| 6,393,316 B1 * | 5/2002 | Gillberg et al. | 600/515 |

* cited by examiner

*Primary Examiner*—George Manuel
(74) *Attorney, Agent, or Firm*—Steven M. Mitchell

(57) ABSTRACT

A system and method for enhancing classification of tachycardias. The tachycardias are associated with a sequence of sensed cardiac complexes, each having a calculated morphology score. The method includes storing intervals corresponding to the sequence of complexes, analyzing the stored intervals, and excluding one or more of the morphology scores based upon the analyzed intervals.

22 Claims, 5 Drawing Sheets

APPARATUS AND METHOD FOR IMPROVED MORPHOLOGY DISCRIMINATION IN AN IMPLANTABLE CARDIOVERTER DEFIBRILLATOR

BACKGROUND OF THE INVENTION

1. Field of the Invention

The present invention relates to improved morphology discrimination (MD) for sensing irregular cardiac rhythms or arrhythmias in an implantable cardioverter defibrillator (ICD).

2. Related Art

ICDs are medical devices that may be surgically implanted in a patient to monitor the patient's cardiac activity and to provide electrical stimulation in order to correct irregular cardiac rhythms (i.e., arrhythmias). The occurrence of the arrhythmias can be attributed to anomalies in the heart's electrical conduction system.

Arrhythmias can generally be thought of as disturbances of the normal rhythm of the heartbeat and can be divided into two major categories: bradyarrhythmia and tachyarrhythmia. Tachyarrhythmia is an abnormally rapid heart rate (e.g., over 100 beats per minute, at rest), while a bradyarrhythmia is an abnormally slow heart rate (e.g., less than 50 beats per minute).

Tachyarrhythmias can be further subdivided into tachycardia and fibrillation. Tachycardia is a condition in which the electrical activity and rhythms of the heart rate are rapid, but organized. Fibrillation, on the other hand, is a condition in which the electrical activity and rhythm of the heart are rapid, chaotic, and disorganized. Tachycardia and fibrillation are further classified according to their location within the heart, namely either ventricular or atrial (supra-ventricular).

A depolarization signal, which is a small electrical impulse, triggers contraction of myocardial tissue within the human heart, causing it to beat. Depolarization signals that correspond to the contraction of the atria are referred to as P-waves, and signals corresponding to the contraction of the ventricles are referred to as R-waves. The complex of depolarization signals produced by a normal heartbeat is commonly referred to as a QRS complex. The sequence of QRS complexes produced by a beating heart creates an electrogram (EGM) or electrocardiogram (ECG) signal (depending upon whether the signal is detected within the heart or on the patient's skin, respectively.) The invention described herein is directed to evaluation of EGMs that can be monitored by appropriate electrical circuitry to determine the condition of the heart. It will be understood by those of skill in the art that the invention is not limited to the location of the sensing electrodes.

A commonly used technique to help discriminate between supra-ventricular and ventricular tachyarrhythmias is morphology discrimination ("MD"). Such a technique is described in U.S. Pat. No. 5,779,645 to Olson et al., which patent is incorporated herein by reference in its entirety. MD techniques use dynamic template matching in order to classify and distinguish complexes associated with supra-ventricular and ventricular tachyarrhythmias. The MD techniques enable an ICD to examine a number of intracardiac electrogram complex characteristics such as amplitude, polarity, and shape, that might be representative of a fast heart rate. The morphology discrimination algorithm then compares each complex with a patient specific template that includes complexes representative of the patient's normal cardiac activity.

Morphology discrimination techniques can operate on the basis of an "X out of Y" system with regard to analyzing a sequence of complexes following detection of a tachycardia. The Y component is representative of the total number of complexes within the sequence, and the X component is representative of the total number of matches out of Y number of complexes necessary to determine that the rhythm is supra-ventricular in origin. A comparison between sensed complexes and the patient specific template is used to determine match or non-match.

In some instances, however, certain cardiac conditions can trigger unacceptably high error rates in classifying arrhythmias as ventricular or supra-ventricular. These errors, due to false classifications, ultimately trigger unnecessary and painful electrical shocks to a patient's heart by the ICD.

The false classification issue was documented in the following abstract: F. Duru, C. Scharf, and C. Brunckhorst et al., "MD Feature in ICDs During Rapid Atrial Pacing and Atrial Fibrillation," Europace 2001; 2: B77 (Abstract 926). This was an acute study involving a series of 20 patients implanted with ICDs evaluated prior to discharge with an electrophysiology study. During that study, incremental atrial pacing was performed at rates of 100, 120, and 140 beats per minute (BPM). Atrial pacing was accomplished via a separate temporary lead inserted into the atrium so that it would not be part of the implanted device. Using the same temporary lead, atrial fibrillation was induced in 17 of the patients.

In this study, the morphology discrimination criteria were set to a 60% match for each complex with a requirement that at least 5 of 8 complexes score greater than 60%. A satisfactory template could be obtained in all patients with MD scores greater than 90% during rest. During incremental rapid atrial pacing, the morphology discrimination feature alone correctly identified the result in ventricular rhythms as being supra-ventricular in 16 of 19 patients for a specificity of 84%. In the group with atrial fibrillation induced, 14 of the 17 were correctly identified as supra-ventricular in origin. In addition, there were isolated beats in four other patients that scored less than a 60% match. Based on the examples included, there were isolated beats with a rate-dependent ventricular aberrant conduction, particularly on the shorter cycles, that accounted for most of the failures to identify, the rhythm as supra-ventricular. There was one example, however, where a commonly used "eyeball" technique failed to demonstrate a discernable difference between the "normal beats" with most of the complexes being scored less than 50%.

Rate-dependent bundle branch block is the most common etiology of the failure of MD techniques to recognize supra-ventricular tachycardias. Failure to recognize supra-ventricular tachycardias is normal behavior of the MD techniques because rate-dependent bundle branch block changes the morphology of the complex from that of the baseline template. There is not a single discriminator that will work in every case.

Other approaches for distinguishing between ventricular and supra-ventricular tachyarrhythmias include techniques such as "sudden onset" and "interval stability." Sudden onset includes monitoring EGM complexes to determine a rate of change the intervals associated with cardiac complexes. For example, when a person exercises, their heart rate typically increases relatively slowly, representing a correspondingly slow rate of change in the associated intervals. During a ventricular episode, however, changes in the heart rate occur much more abruptly. The sudden onset technique attempts to use this abruptness as a characteristic to distinguish ventricular episodes from supra-ventricular episodes.

Interval stability entails monitoring and analyzing ventricular to ventricular (R—R) intervals. Although morphology discrimination, sudden onset, and interval stability are somewhat successful in distinguishing between ventricular and supra-ventricular tachyarrhythmias, more reliable techniques are needed.

By way of background, the conduction system of the heart includes an AV node, which serves as a buffer between the atrium (upper chamber) and the ventricle (lower chamber) of the heart. Specifically, the AV node controls the transmission of electrical impulses (originating in the upper chamber) from the upper chamber to the lower chamber. There are some rhythms in the upper chambers that are inherently fast. And while these fast rhythms, or high atrial rates, are not consistent with optimized cardiac performance, they are not lethal.

During cases of high atrial rates, the buffering provided by the AV node prevents some of the electrical impulses in the atrium from reaching the ventricle such that although the atrium might be beating rapidly, the ventricle might not beat quite as rapidly. Although the buffering provided by the AV node prevents transmission of most of the electrical impulses from the atrium to the ventricle, some impulses actually get through, making the ventricular rhythms appear faster. Fast rhythms in the lower chambers of the heart, however, can be lethal. Therefore, it is important to know whether any fast ventricular rhythms actually originate in the ventricle, or are caused by rhythms that originated in the atria.

One way the AV node provides buffering is that it slows down some fast-rate impulses while causing others to completely drop out. In some cases, these fast supra-ventricular rhythms create corresponding changes in the rates of the ventricular rhythms. At the same time, however, these fast rate supra-ventricular impulses cause the morphology of the associated QRS complexes to resemble normal complexes. Therefore, in these cases, the supra-ventricular rhythms can be effectively distinguished from the ventricular rhythms using morphology discrimination. In other cases, however, the supra-ventricular rhythms create distortion in the morphology of the ventricular QRS complexes, creating errors in the morphology discrimination analysis. One of the conditions that triggers these errors is known as variable conduction. It has also been noted that these variable conduction supra-ventricular rhythms are typically characterized by short R—R intervals, which create the mis-match between the ventricular QRS complexes and the sinus template.

What is needed therefore is an improved morphology discrimination technique to more accurately classify supra-ventricular complexes created due to conditions such as variable conduction.

SUMMARY OF THE INVENTION

Consistent with the principles of the present invention as embodied and broadly described herein, an exemplary technique includes a method for improving classification of rhythms produced by a beating heart. The rhythms are associated with a sequence of complexes for which morphology scores are calculated. The method comprises storing intervals corresponding to the sequence of complexes and analyzing the stored intervals. Finally, one or more of the morphology scores may be excluded based upon the analyzed intervals.

In summary, the present invention is an enhancement to existing techniques, such as morphology discrimination, that distinguish between ventricular and supra-ventricular tachyarrhythmias. Morphology discrimination, for example, is based upon the knowledge that EGM complexes associated with supra-ventricular tachyarrhythmias have morphological characteristics that are substantially similar to sinus EGMs. Ventricular tachyarrhythmias, on the other hand, have their own unique morphological characteristics. Thus, although a particular fast-rate episode may initially be identified as ventricular in origin, an analysis of the morphology of its associated EGM complexes may convey a different story.

An EGM complex analysis based upon application of a morphology discrimination technique produces a resulting MD score for each complex. In order to reduce energy consumption from the device battery, this is preferably performed only on those complexes that are part of the sequence of complexes that triggered tachycardia detection. A high MD score indicates that the tachyarrhythmia complex closely matches the patient's sinus template, indicating that the episode is likely supra-ventricular. A low score typically indicates that the complex does not match the patient's sinus template, normally indicating, based upon the unique morphology of the sequences, that the episode is ventricular. The problem, however, is that under certain conditions complexes associated with supra-ventricular episodes can become sufficiently distorted such that although the complexes are otherwise normal, they nonetheless fail to match the patient's sinus template, thus triggering erroneous non-matches. One of the conditions that triggers this occurrence is variable conduction, which is a by-product of rate-related bundle branch block. During rate-related bundle branch block, the morphological distortion of otherwise normal complexes associated with supra-ventricular tachyarrhythmias, diminishes the reliability of the MD score.

The inventor of the instant invention, however, has discovered that these distorted complexes have identifiable and distinguishing characteristics. One of the distinguishing characteristics is that these normal, although distorted, supra-ventricular complexes are preceded by an irregular short interval—even shorter than the naturally short intervals that comprise the tachyarrhythmia. The present invention thus facilitates the identification and subsequent exclusion of these irregular short interval complexes from the MD score. By excluding these short interval complexes from the MD score, the present invention enables the morphology discrimination technique to more accurately determine whether the tachyarrhythmia is ventricular or supra-ventricular.

Therefore, the present invention enhances the ability of existing techniques, such as morphology discrimination, to distinguish between the less serious supra-ventricular tachyarrhythmias and their potentially lethal ventricular counterparts. This distinction enables the implanted device to more accurately discriminate between ventricular and supra-ventricular tachycardias and more appropriately determine when ventricular tachycardia therapy is required, thus providing less discomfort and an overall higher level of care for the cardiac patient.

Further embodiments, features, and advantages of the present invention, as well as the structure and operation of the various embodiment of the present invention, are described in detail below with reference to the accompanying drawings.

BRIEF DESCRIPTION OF THE FIGURES

The accompanying drawings, which are incorporated and constitute a part of the specification, illustrate an embodiment of the invention and, together with the description, explain the purpose, advantages, and principles of the invention.

DETAILED DESCRIPTION OF THE PREFERRED EMBODIMENTS

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. The invention is not limited to any specific software or hardware that is described herein. Furthermore, the operation and behavior of the present invention will be described with the understanding that modifications and variations of the embodiments are possible, given the level of detail presented herein.

Figure 1A:
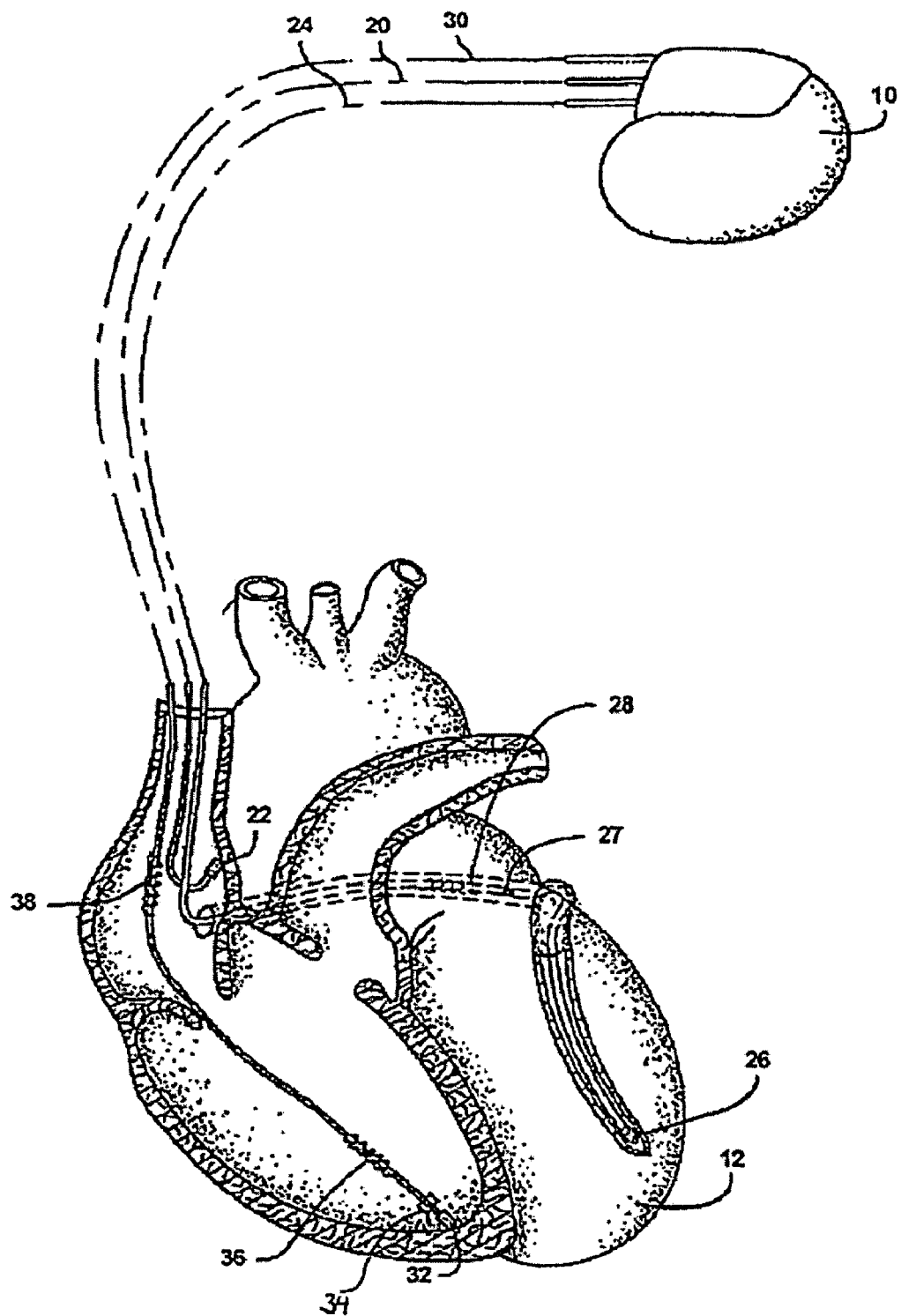
FIG. 1A is a simplified diagram illustrating an implantable stimulation device in electrical communication with at least three leads implanted into a patient's heart for delivering multi-chamber stimulation and shock therapy.
Figure 1B:
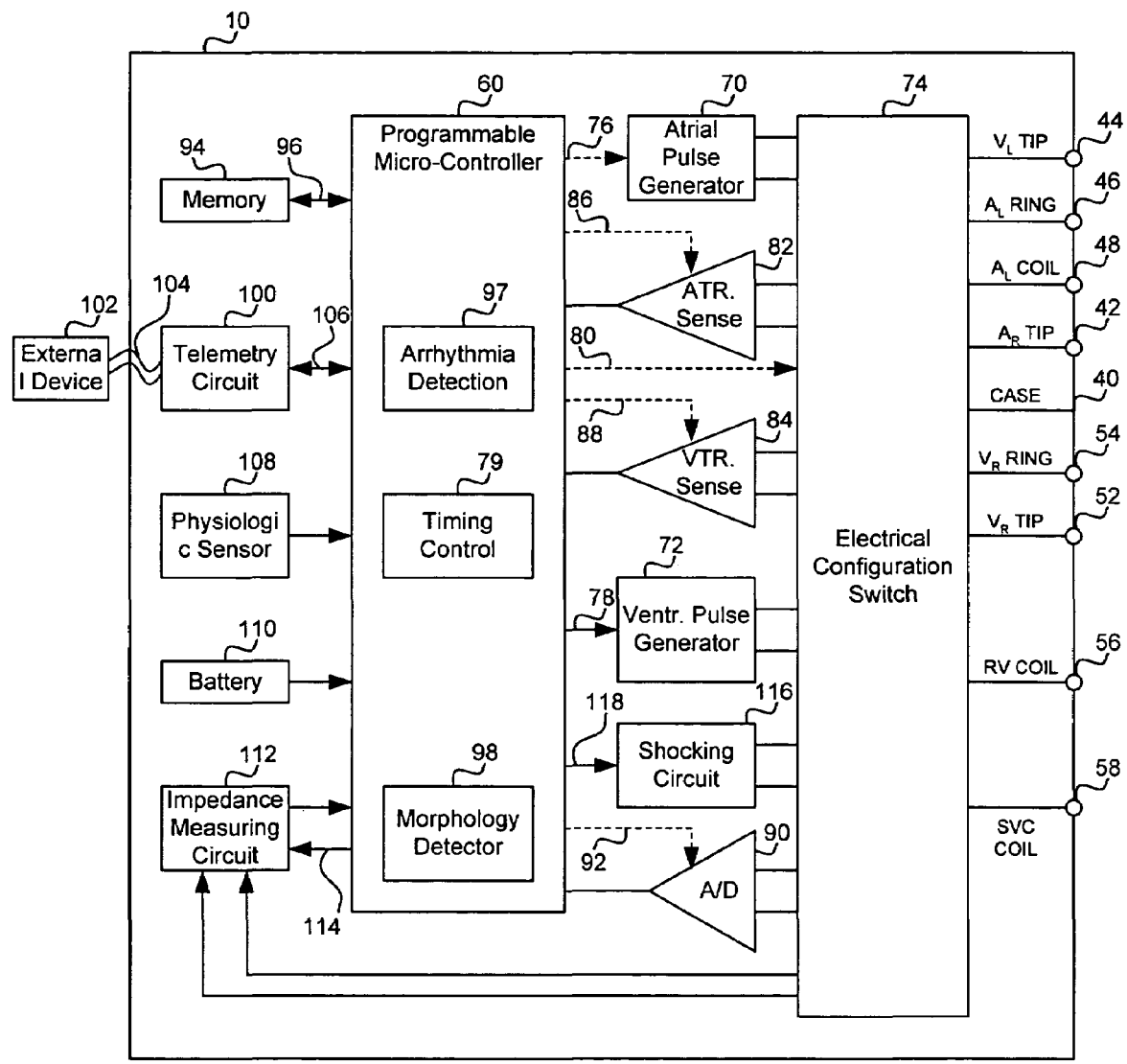
FIG. 1B is a functional block diagram of a multi-chamber implantable stimulation device illustrating the basic elements of a stimulation device which can provide cardioversion, defibrillation and pacing stimulation in four chambers of the heart.

Before describing the invention in detail it is helpful to describe an example environment of which the invention may be implemented. The present invention is particularly useful in the environment of an ICD. FIGS. 1A and 1B illustrate such an environment.

In FIG. 1A, an exemplary stimulation device 10 (also referred to as a pacing device, or a pacing apparatus) is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. Although the device 10 is shown as having three leads, the present invention is not limited to such a device.

To sense left atrial and ventricular cardiac signals and to provide left-chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

As illustrated in FIG. 1B, a simplified block diagram is shown of the multi-chamber stimulation device 10, which is capable of treating both fast and slow arrhythmias with stimulation therapy, including cardioversion, defibrillation, and pacing stimulation. While a particular multi-chamber device is shown, its showing is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 1B, is often referred to as the "can," "case" or "case electrode" and may be programmably selected to act as the return electrode for all "unipolar" modes. The housing 40 may further be used as a return electrode alone or in combination with one or more of the coil electrodes, 28, 36, and 38 for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing, and shocking the connector also includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are configured for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design of the microcontroller 60 are not critical to the present invention. Rather, any suitable microcontroller 60 can be used to carry out the functions described herein. The use of microprocessor-based control circuits for performing timing and data analysis functions are well known in the art. In specific embodiment of the present invention, the microcontroller 60 performs some or all of the steps associated with determining optimal pacing parameters in accordance with the present invention.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 1B, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control pacing parameters (e.g. the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular (AV) delay, interventricular (RV-LV) delay, atrial pacing rate (A—A), and ventricular pacing rate (V—V).

Finally, the microcontroller 60 includes an arrhythmia detection mechanism 97 and a morphology detector 98. The arrhythmia detection mechanism 97 is provided to detect the occurrence of fast rate cardiac episodes, such as tachycardias, which are rapid (typically greater than 150 BPM) but disorganized rhythms. The morphology detector 98 is provided to assess characteristics such as amplitude, polarity, and shape, of detected cardiac rhythms.

The switch bank-74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR SENSE) and ventricular (VTR SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. Such sensing circuits, 82 and 84, can be used to determine cardiac performance values used in the present invention.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, in the appropriate chambers of the heart. The sensing circuits, 82 and 84, in turn, receive control signals over signal lines, 86 and 88, from the microcontroller 60 for purposes of measuring cardiac performance at appropriate times, and for controlling the gain, threshold, polarization charge removal circuitry (not shown), and timing of any blocking circuitry (not shown) coupled to the inputs of the sensing circuits, 82 and 86.

For arrhythmia detection, the device 10 utilizes the atrial and ventricular sensing circuits, 82 and 84, to sense cardiac signals to determine whether a rhythm is physiologic or pathologic. The timing intervals between sensed events (e.g., the P-waves. R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote. Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to an external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In the preferred embodiment, the stimulation device 10 further includes a physiologic sensor 108, which can be used to detect changes in cardiac performance or changes in the physiological condition of the heart. Accordingly, the microcontroller 60 can respond by adjusting the various pacing parameters (such as rate, AV Delay, RV-LV Delay, V—V Delay, etc.) in accordance with the embodiments of the present invention. The microcontroller 60 controls adjustments of pacing parameters by, for example, controlling the stimulation pulses generated by the atrial and ventricular pulse generators, 70 and 72. While shown as being included within the ICD 10, it is to be understood that the physiologic sensor 108 may also be external to the stimulation device 10, yet still be implanted within or carried by the patient. More specifically, the sensor 108 can be located inside the device 10, on the surface of the device 10, in a header of the device 10, or on a lead (which can be placed inside or outside the bloodstream).

The stimulation device 10 additionally includes a battery 110 which provides operating power to all of the circuits shown in FIG. 1B. For the ICD 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to disable therapy of the stimulation device 10 and/or to signal the microcontroller 60 that the external programmer 102 is in place to receive or transmit data to the microcontroller 60 through the telemetry circuits 100.

As further shown in FIG. 1B, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown only for completeness.

In the case where the stimulation device 10 is intended to operate as an ICD, it must detect the occurrence of an arrhythmia, and automatically apply an appropriate electrical therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally of a low to moderate energy level (so as to minimize pain felt by the patient), synchronized with an R-wave, and pertain to the treatment of tachycardias. In contrast, defibrillation shocks are generally of a moderate to high energy level (i.e., corresponding to thresholds in the range of 5–40 Joules), delivered asynchronously (since R-waves may be too disorganized to be recognized), and pertaining exclusively to the treatment of fibrillation. Accordingly, the microcontroller 60 is capable of controlling the synchronous or asynchronous delivery of shocking pulses of varying duration and amplitude.

The present invention provides an improvement to traditional morphology discrimination techniques by enhancing their ability to more accurately classify arrhythmias, such as tachycardias. As stated above, the inventors of the instant invention have discovered a consistent difference between the morphology of QRS complexes associated with rate-related bundle branch block, which generate low MD scores, and complexes produced by normal sinus rhythms, which generate higher MD scores. One such difference is that groups of fast-rate complexes associated with rate-related bundle branch block are often preceded by a short R—R interval, as shown in FIG. 2.

Figure 2:
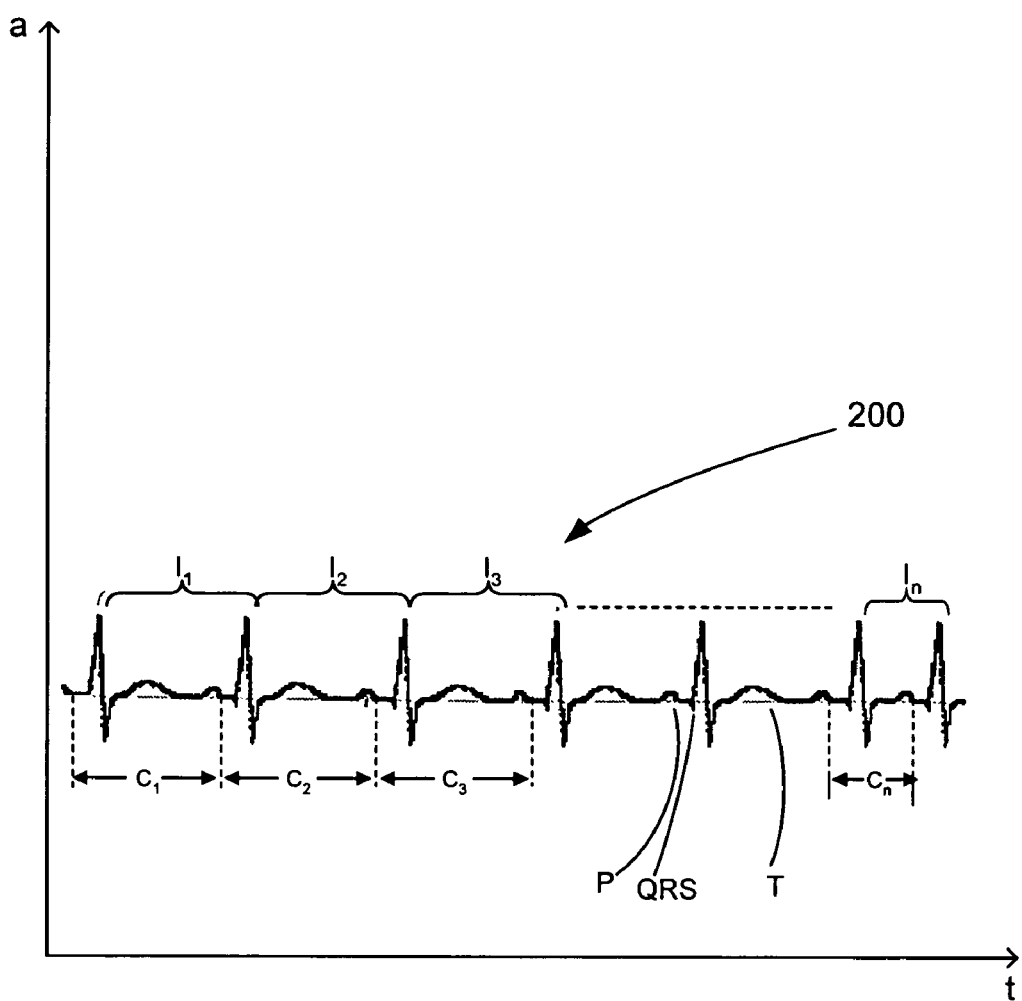
FIG. 2 is a timing diagram illustrating a sequence of complexes having at least one short interval.

FIG. 2 is a timing diagram, or ECG, illustrating PQRS complexes 200 having at least one short interval. The complexes 200 are presented herein as illustration of an exemplary ECG that might be observed during a supra-ventricular tachycardia. Although the complexes 200 of FIG. 2 shown here for purposes of illustration are representative of a surface ECG, the present invention is primarily directed to analysis of intracardiac EGMs but the invention is not limited to either application. The present invention detects the relatively shorter interval during a tachycardia, thus providing a basis to associate its related QRS complex with other supra-ventricular complexes. As noted above, the misidentification of supra-ventricular fast rhythms by traditional morphology discrimination techniques may trigger unnecessary and uncomfortable patient shocks by the ICD.

In FIG. 2, a sequence of complexes 200 produced by a beating heart is graphically illustrated having indices representative of time (t) and amplitude (a). The sequence of complexes 200 includes a number of individual complexes $C_1$–$C_n$ that are each representative of one beat of the human heart. As discussed above, each complex includes three major waves of electric energy that typically appear on an ECG. Each wave illustrates a different segment of the heartbeat and includes the P-wave, the QRS wave, and a T-wave, shown in FIG. 2.

The sequence of complexes $C_1$–$C_n$ includes a corresponding sequence of R—R intervals $I_1$–$I_n$. Each of the corresponding intervals is measured from a peak of one QRS complex to the peak of the ensuing QRS complex. As also illustrated, each of the corresponding intervals $I_1$–$I_3$ are substantially the same length. The sequence of complexes 200 also includes a short interval $I_n$, that might be indicative of a distorted complex occurring during a supra-ventricular tachycardia.

In a normal heartbeat, an exemplary length of the intervals $I_1$–$I_3$ might be on the order of about 750 milliseconds (ms), corresponding to a heart rate of 80 BPM. During a tachycardia, the intervals $I_1$–$I_3$ might be closer to 400 ms, corresponding to a heart rate of 150 BPM. During a supra-ventricular tachycardia, however, the short interval $I_n$ might be on the order of 200–300 milliseconds. Therefore, a greater number of particular ones of the complexes 200 can be distinguished from ventricular complexes and thereby associated with supra-ventricular complexes on the basis or presence of one or more irregular short intervals, such as the short interval $I_n$.

Figure 3:
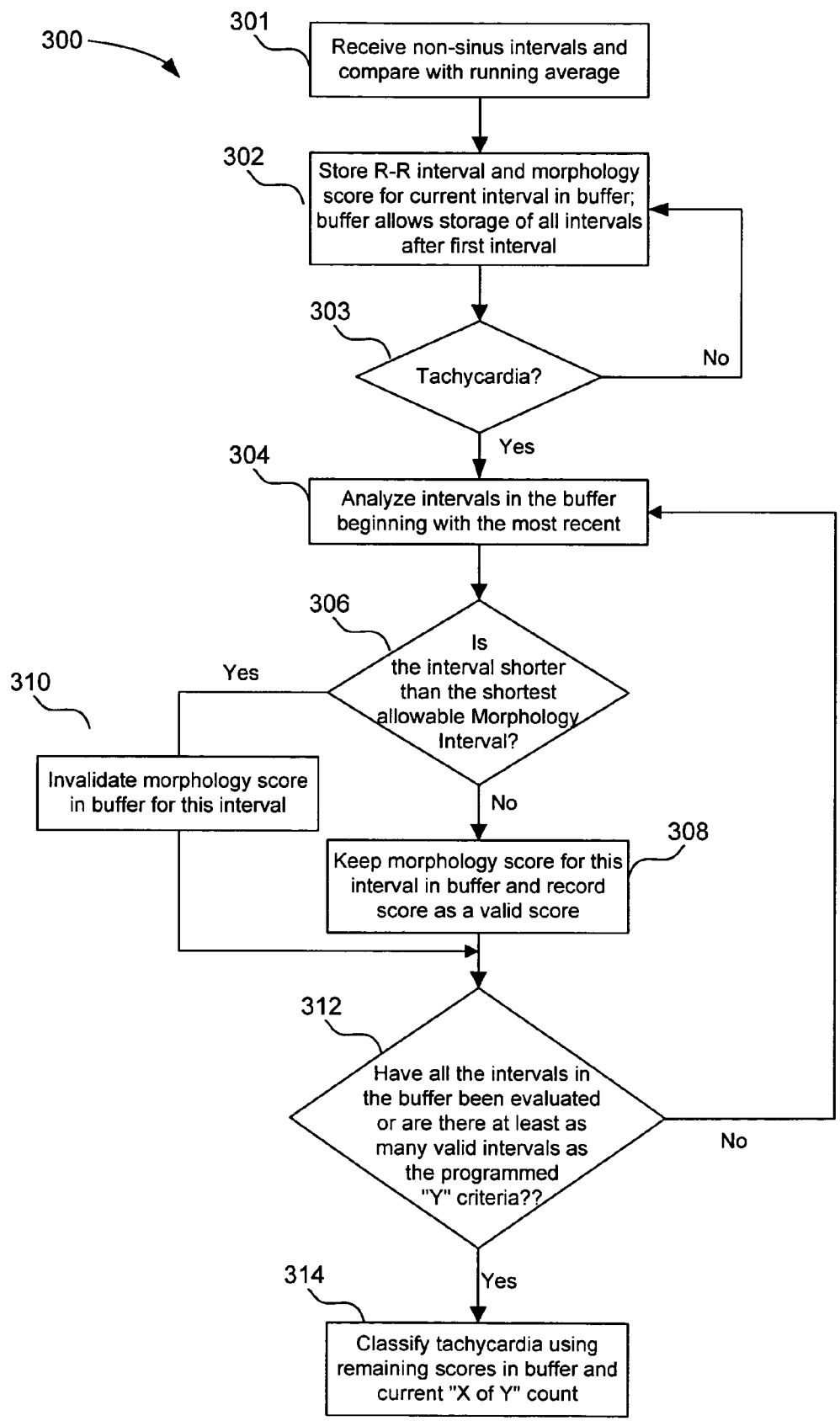
FIG. 3 is a flowchart of a method for classifying rapid heart rhythms.

FIG. 3 is a flowchart 300 representative of an exemplary embodiment of the present invention that distinguishes complexes on the basis of interval lengths such as the short interval $I_n$. An important advantage of the present invention is the ability to be able to more clearly distinguish between life-threatening, but treatable arrhythmias, such as tachycardias and non life-threatening supra-ventricular tachycardias.

During activation of the instant invention, the microcontroller 60 is configured to operate as a filter in order to only receive non-sinus intervals (within the tachycardia zone) as inputs. The tachycardia zone is representative of fast (150–200 BPM), but very organized rhythms. The controller 60, therefore, provides a cutoff point so that only R—R intervals corresponding to the exemplary range of about 150–200 BPM can be received. Next, using conventional morphology discrimination techniques, the MD score of an exemplary tachycardia complex, such as the complex 200, can be determined (not shown). As discussed in greater detail below, the present invention then analyzes the complexes associated with the MD score by identifying short R—R intervals and excludes the scores associated with these short intervals.

In block 301, the exemplary device 10, using conventional techniques, receives non-sinus intervals and compares the received intervals with a running average of all received intervals. The comparison provides compensation for minor variations in the received intervals in order to ensure that a potential fast-rate cardiac episode is indeed a non-sinus interval and not a system hiccup that merely produces one or two extraneous non-sinus type intervals. Averaging can occur, for example, over the last four intervals or any other suitable number deemed appropriate by the physician.

In block 302, the first non-sinus R—R interval is received but is not stored. Reception of the first received non-sinus R—R interval, however, activates the interval storage circuitry (not shown) of the device 10, facilitating storage of all subsequently received non-sinus R—R intervals in the memory 94. The MD score associated with the non-sinus R—R intervals is also stored in the memory 94. Since interval storage circuitry typically consumes valuable power resources, the storage circuitry is not continuously on, but instead, is only activated after reception of the first non-sinus interval. Although any suitable number of intervals can be chosen, typically at least 10 to 12 intervals are required to be stored in order to ensure optimal operation of the technique of the present invention.

In block 303, the micro-controller 60 is configured to determine whether the received R—R intervals indicate the occurrence of a tachycardia. If a tachycardia is not occurring, the block 303 returns to block 302 where the next R—R interval and MD score are stored in the memory 94. If device 10 determines a tachycardia is occurring, the micro-controller 60 analyzes all of the stored R—R intervals, beginning with the most recently stored interval, as indicated in block 304 of FIG. 3.

In block 306, it is determined whether the current interval is shorter than a shortest allowable morphology interval length. The shortest allowable morphology interval length is a threshold that is apriorily determined and set by the attending physician. This threshold can be set to a finite length, such as 200 ms, or can be set as a percentage of an average interval value. If the current interval is not shorter than the shortest allowable morphology interval (threshold), the MD score for that particular interval is retained in the memory 94 and is recorded as a valid score, as indicated in block 308.

On the other hand, if the current interval is shorter than the threshold, its MD score, presently stored in the memory 94, is invalidated, as indicated in block 310. Consider the example where the MD discrimination criteria is set at greater than 60% and 5 of 8 complexes (meaning that at least 5 of the most recent 8 complexes must match the patient's sinus template each with a score greater than 60%). Next, assume the score of the complex associated with the current interval is 50%, meaning that it is not a match with the template. Also, assume that the most recent 7 complexes in the buffer have been evaluated with 4 of 7 complexes meeting the MD discrimination criteria and the failure of the 8th complex to satisfy the criteria would result in a count of 4 of 8. In this example, the present invention would invalidate the 50% score and an additional complex would be evaluated.

In block 312, the micro-controller 60 determines whether all of the intervals in the memory 94 have been analyzed or whether a sufficient number of intervals have been examined to satisfy the Y count (Y criterion) of the X out of Y criteria. If all of the intervals in the buffer have not been examined, and the Y criterion has not been satisfied, the technique 300 returns to block 304 and additional intervals are then analyzed.

Finally, as indicated in block 314, the MD scores in the memory 94 are analyzed based upon the new X of Y count, as amended based upon block 310 to classify the tachycardia. Thus, the technique 300 minimizes the effects of variable conduction caused by rate-related bundle branch block, enhancing the overall accuracy of the MD score.

Figure 4:
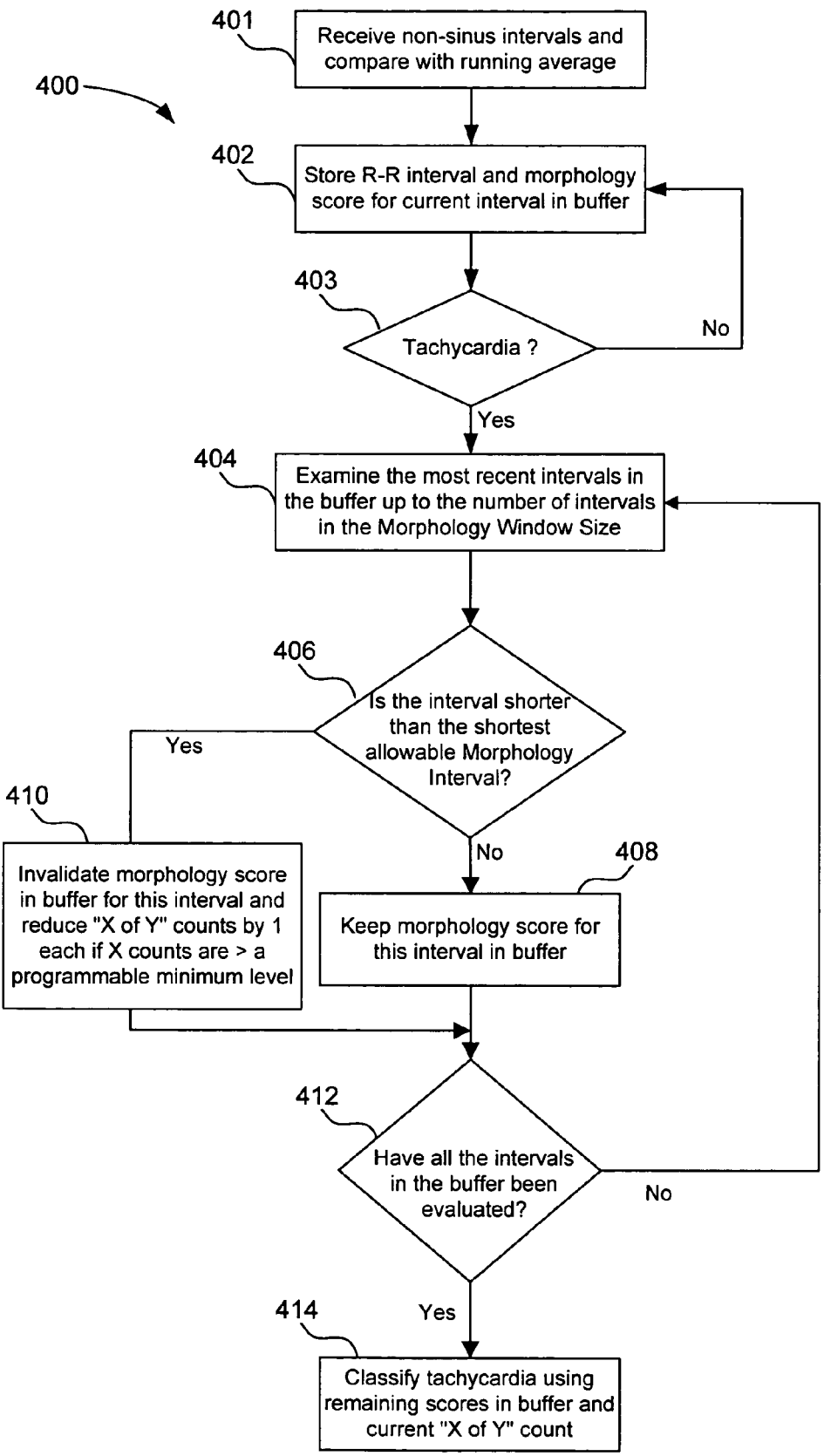
FIG. 4 is a flowchart of an alternative embodiment of the technique shown in FIG. 3.

FIG. 4 is an illustration of an alternative embodiment of the technique 300, shown in FIG. 3. In FIG. 4, a technique 400 operates similar to the technique 300 of FIG. 3. The technique 400, however, does not include a requirement to store all of the R—R intervals following the first non-sinus interval. In the technique 400, the only requirement is that a sufficient number of R—R intervals be stored to satisfy the Y criterion of the X of Y count. For example, if the X of Y count requirement is 5 of 8 complexes, then only 8 intervals are required to be stored, as indicated in block 402. After a tachycardia determination has been made, as indicated in block 403, the most recent intervals in the memory 94 are examined up to the morphology window size (the Y criterion), as indicated in block 404.

Next, in block 406, it is determined whether the current interval, within the analyzed intervals, is shorter than the shortest allowable morphology interval, as performed in block 306 of FIG. 3. If the interval is not shorter than the shortest allowable interval, the MD score for the current interval is retained in the memory 94, as indicated in block 408.

If on the other hand, the current interval is shorter than the shortest allowable morphology interval, the morphology score is invalidated. In the embodiment of FIG. 4, however, both of the X and Y components of the X of Y criteria are reduced by a count of one for each interval that is invalidated. Thus, if the initial criterion was set to 5 of 8, after the first interval is invalidated, the requirement becomes 4 of 7. If a second interval is invalidated, the requirement becomes 3 of 6, etc. The attending physician will determine the minimum required X count, such that the technique 400 does not reach an unacceptable criteria, such as 0 of 3. If the X count is above this programmable minimum level, as indicated in block 410, the technique 400 determines whether all of the intervals have been evaluated, as required in block 412.

Finally, the MD score is evaluated based upon the current X of Y count, as indicated in block 414 to classify the tachycardia. If all of the intervals have not been evaluated then the process returns to block 404 and additional intervals are evaluated.

By enhancing the accuracy of existing discrimination techniques, such as morphology discrimination, the present invention compensates for short intervals that can be attributed to variable conduction, caused by rate-related bundle branch block. The net result is a more accurate MD score that will ultimately facilitate better discrimination between ventricular and supra-ventricular arrhythmias and consequently less discomfort to the patient.

The foregoing description of the preferred embodiments provides an illustration and description, but is not intended to be exhaustive or to limit the invention to the precise form disclosed. Modifications and variations are possible consistent with the above teachings, or may be acquired from practice of the invention.

We claim:

1. A method for improving classification of rhythms produced by a beating heart, the rhythms being associated with a sequence of QRS complexes, each complex having a morphology score based on a comparison of the complex to a template, the method comprising:
   (a) storing intervals corresponding to the sequence of complexes;
   (b) analyzing the stored intervals; and
   (c) excluding one or more of the morphology scores from a rhythm classification based upon the analyzed intervals.

2. The method of claim 1, wherein the rhythm is a tachycardia.

3. The method of claim 2, wherein the stored intervals are R—R intervals.

4. The method of claim 3, further comprising the step of:
   (d) distinguishing between ventricular and supra-ventricular tachycardias based in part on said excluding step.

5. The method of claim 4, wherein said analyzing step comprises determining a length of each of the stored intervals; and
   comparing the determined length with a threshold value.

6. The method of claim 5, wherein the threshold value is a percentage of an average length of the stored intervals.

7. The method of claim 5, wherein the threshold value is a predetermined length.

8. The method of claim 5, wherein said analyzing step further comprises determining whether the length of the current interval is shorter than the threshold value.

9. The method of claim 8, wherein the distinguishing step includes determining if a predetermined number of complexes of a total number of required complexes (X of Y) have a morphology score greater than a predetermined threshold; and
   wherein step (c) includes not altering the value of X or Y associated with the current interval when the current interval length is shorter than the predetermined length.

10. The method of claim 8, wherein the distinguishing step includes determining if a predetermined number of complexes of a total number of required complexes (X of Y) have a morphology score greater than a predetermined threshold; and
   wherein step (c) includes decrementing the value of X and Y when the current interval length is shorter than the predetermined length.

11. A method for enhancing classification of arrhythmias using an implantable cardioverter defibrillator having a memory, the arrhythmia including a sequence of complexes, the method comprising:
   storing intervals corresponding to the time between sensed complexes in the memory;
   detecting a tachycardia;

comparing each of the complexes in the sequence with a template to generate a morphology score for each complex;
analyzing the stored intervals when the tachycardia is detected;
determining whether a selected one of the stored intervals is shorter than a predetermined length;
invalidating a morphology score for a complex corresponding to the selected interval if the length of the selected interval is shorter than the predetermined length; and
diagnosing the type of tachycardia based on the remaining valid morphology scores.

12. The method of claim 11, wherein the predetermined length is indicative of a shortest allowable morphology interval.

13. The method of claim 11, further comprising a step after said determining step of:
retaining the morphology score of the complex corresponding to the selected interval if the length of the selected interval is not shorter than the predetermined length.

14. The method of claim 13, wherein the diagnosing step includes determining if a predetermined number of complexes of a total number of required complexes (X of Y) have a morphology score greater than a predetermined threshold.

15. A computer readable medium carrying one or more sequences of one or more instructions for execution by one or more processors to perform a method for enhancing classification of a tachycardia using an implantable cardioverter defibrillator having a memory, the arrhythmia including a sequence of complexes, the instructions when executed by the one or more processors causing the one or more processors to perform the steps of:
storing R—R intervals in the memory, each interval corresponding to a subsequent complex;
detecting a tachycardia;
analyzing the stored intervals when the tachycardia is detected;
determining whether a selected one of the stored intervals is shorter than a predetermined length;
invalidating the complex corresponding to the selected interval if the length of the selected interval is shorter than the predetermined length;
calculating a morphology score based on a comparison to a template for at least each complex not invalidated; and
classifying the tachycardia based on the morphology scores of complexes not invalidated.

16. The computer readable medium of claim 15, wherein the predetermined length is indicative of a shortest allowable morphology interval.

17. The computer readable medium of claim 15, further causing the one or more processors to retain the morphology score corresponding to the selected interval if the length of the selected interval is not shorter than the predetermined length.

18. An apparatus configured to enhance classification of a tachycardia, the apparatus comprising:
means for sensing a sequence of cardiac complexes;
means for measuring and storing a sequence of R—R intervals between successive complexes, each interval corresponding to a subsequent complex;
means for detecting a tachycardia based on the measured intervals;
means for analyzing the stored intervals when the tachycardia is detected;
means for determining whether a selected one of the stored intervals is shorter than a predetermined length;
means for ignoring the complex corresponding to the selected interval if the length of the selected interval is shorter than the predetermined length; means for calculating a morphology score based on a comparison to a template for at least each complex not ignored; and
means for classifying the tachycardia based on the morphology scores of complexes not ignored.

19. A method for improving classification of a tachycardia, the tachycardia being associated with a sequence of complexes, each complex having a calculated morphology score, comprising the steps of:
storing intervals corresponding to the sequence of complexes;
analyzing the stored intervals; and
excluding one or more of the morphology scores from a rhythm classification based upon the analyzed intervals.

20. The method of claim 19 wherein the analyzing step includes comparing the stored intervals to an interval threshold.

21. The method of claim 20 and further including the step of classifying a tachycardia as ventricular or supra-ventricular by analyzing the morphology scores not excluded.

22. An apparatus for improving classification of rhythms produced by a beating heart, the rhythms being associated with a sequence of complexes, each complex having a calculated morphology score, the apparatus comprising:
means for storing intervals corresponding to the sequence of complexes;
means for analyzing the stored intervals; and
means for excluding one or more of the morphology scores from a rhythm classification based upon the analyzed intervals.

* * * * *